Dec. 12, 1961 T. VAN DER SCHILDEN Plant Pat. 2,109
ROSE PLANT
Filed Dec. 20, 1960
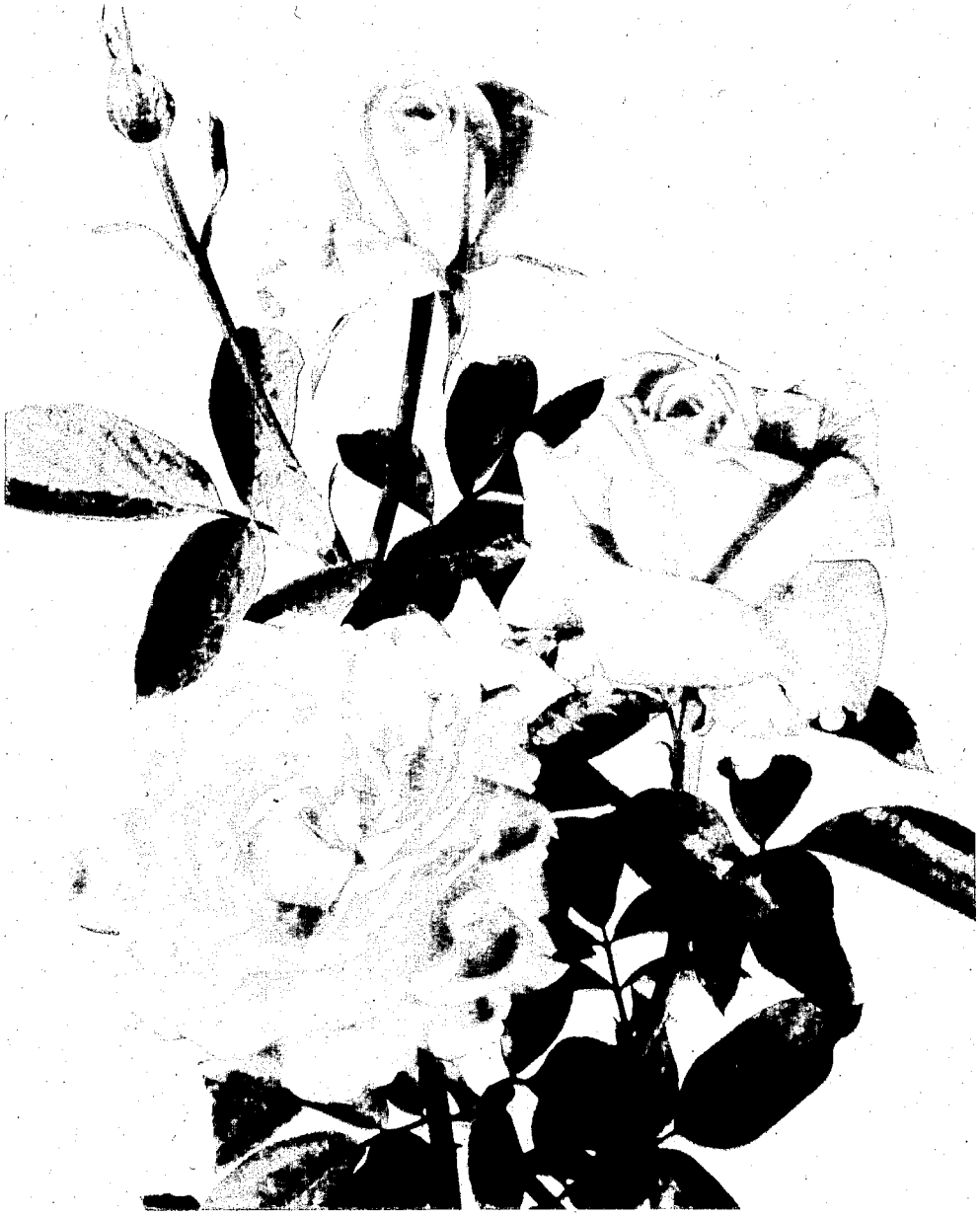
Inventor.
Teunis van der Schilden
By: Robb & Robb
Attorneys.

United States Patent Office

Plant Pat. 2,109
Patented Dec. 12, 1961

2,109
ROSE PLANT

Teunis van der Schilden, Aalsmeer, Netherlands, assignor to Armstrong Nurseries, Inc., Ontario, Calif., a corporation of California Filed Dec. 20, 1960, Ser. No. 77,257
1 Claim. (Cl. 47—61)

The present invention relates to a new and distinct variety of rose plant of a class between the hybrid tea and floribunda classes, which was discovered by me as a cultivated sport of the variety known as "Montezuma" (U.S. Plant Patent No. 1,383).

This new variety was discovered by me in my greenhouse at Aalsmeer, Holland, where I was growing plants of the parent variety "Montezuma." At the time of my discovery aforementioned, my attention was attracted to one particular plant amongst those of the variety "Montezuma" by the fact that the plant bore flowers that were brighter and distinctly different in color from the normal flower color of the variety "Montezuma." Upon closer examination of this plant, I found that it had sported, and I thereupon took steps to preserve the sport, kept it under observation, and later asexually reproduced the same. My continued observations of the original plant and the asexually reproduced progeny thereof, as produced by me by grafting at Aalsmeer, Holland, and also as performed on my behalf by budding at Ontario, California, U.S.A., fully confirmed the new flower characteristics of the sport and conclusively established that these characteristics come true to form and are transmissible through succeeding propagations.

My new variety is essentially distinguished from its parent "Montezuma" by having a brighter and more distinctly orange tone in the general color tonality of the flowers. The general color effect of the newly opened flowers of the variety "Montezuma" is near Geranium Lake, whereas the flowers of my new variety have a general color effect between Mandarin Red and Vermilion in the newly open stage, which later becomes between Vermilion and Scarlet without the usual bluing effect of the flowers of "Montezuma" and, consequently, resulting in a brighter flower color, and a more orange appearance.

Other than the difference in the color of the flowers of my new variety, as noted in the foregoing, it is substantially identical to its parent "Montezuma."

The accompanying drawing shows typical specimens of the flowers and foliage of my new variety in different stages of development and as depicted in color as nearly true as it is reasonably possible to make the same in a color illustration of this character.

In view of the similarities between the new variety and its parent, excepting for the color difference in the flowers, it is unnecessary to describe the new variety in complete detail, since it generally conforms to the description appearing in U.S. Plant Patent No. 1,383, issued April 19, 1955, to which reference may be readily had. However, for convenience, the following description is given of the flower color and other basic details of the new variety, with color terminology in accordance with Robert F. Wilson's Horticultural Colour Chart:

Type: Bush; outdoor; sport; for cut flowers and for garden decoration.

Class: Between the hybrid tea and floribunda classes.

Parentage: Sport of "Montezuma."

Propagation: Holds its distinguishing characteristics through succeeding propagations by both grafting and budding.

*Flower*

(Observations made from specimens grown at Ontario, California, U.S.A.)

Bud:

*As calyx breaks.*—Color—between Oxblood Red, Plate 00823/3, page 191, and Delft Rose, Plate 020/2, page 108.

*As first petal opens.*—Color: outside—between Scarlet, Plate 19/2, page 19, and Geranium Lake, Plate 20/1, page 20, with small area at base of petal near attachment near Uranium Green, Plate 63/2, page 63; inside—between Vermilion, Plate 18, page 18, and Scarlet, Plate 19/1, page 19, with small area at base near attachment near Uranium Green, Plate 63/2, page 63.

This description of a newly opened flower was made from a rose grown outdoors during the month of August at Ontario, California, U.S.A.:

*Color.*—Outer pedal: outside surface—between Scarlet, Plate 19/2, page 19, and Geranium Lake, Plate 20/1, page 20, with small area at base near attachment near Uranium Green, Plate 63/3, page 63; inside surface—between Vermilion, Plate 18/1, page 18, and Scarlet, Plate 19/1, page 19, with small area at base near attachment near Uranium Green, Plate 63/3, page 63. Intermediate petal: outside surface—between Scarlet, Plate 19/2, page 19, and Geranium Lake, Plate 20/1, page 20, with small area at base near attachment near Uranium Green, Plate 63/3, page 63; inside surface—near Vermilion, Plate 18/1, page 18, with small area at base near attachment near Uranium Green, Plate 63/3, page 63. Inner petal: outside surface—between Vermilion, Plate 18/1, page 18, and Scarlet, Plate 19/2, page 19, with small area at base near attachment near Uranium Green, Plate 63/3, page 63; inside surface—between Mandarin Red, Plate 17/1, page 17, and Vermilion, Plate 18/2, page 18, with small area at base near attachment near Uranium Green, Plate 63/3, page 63.

This description was made from a rose that was open for three days outdoors during the month of August at Ontario, California, U.S.A.:

*Color.*—Outer petal: outside surface—between Scarlet, Plate 19/1, page 19, and Geranium Lake, Plate 20/1, page 20, with small area at base near attachment near Dresden Yellow, Plate 64/3, page 64; inside surface—between Vermilion, Plate 18/2, page 18, and Scarlet, Plate 19/1, page 19, with small area near attachment near Dresden Yellow, Plate 64/3, page 64. Inner petal: outside surface—between Scarlet, Plate 19/2, page 19, and Geranium Lake, Plate 20/2, page 20, with small area at base near attachment near Dresden Yellow, Plate 64/3, page 64; inside surface—between Vermilion, Plate 18/2, page 18, and Scarlet, Plate 19/1, page 19, with small area at base near Dresden Yellow, Plate 64/3, page 64.

*General color effect.*—Newly opened flower—between Mandarin Red, Plate 17/1, page 17, and Vermilion, Plate 18/1, page 18. 3-days open—between Vermilion, Plate 18/2, page 18, and Scarlet, Plate 19/1, page 19.

I claim:

A new and distinct variety of rose plant of a class between the hybrid tea and floribunda classes, substantially as herein shown and described, characterized particularly as to novelty by being generally similar to its parent variety "Montezuma" (U.S. Plant Patent No. 1,383), but being essentially distinguished therefrom by a brighter and more distinctly orange tone in the general color tonality of its flowers, said general color tonality being between Mandarin Red and Vermilion in the newly open flower stage and later becoming between Vermilion and Scarlet, without the usual bluing effect of the flowers of "Montezuma" and, consequently, resulting in a brighter flower color and a more orange appearance.

No references cited.